United States Patent [19]

Shofner et al.

[11] 4,389,574

[45] Jun. 21, 1983

[54] METHOD AND APPARATUS FOR DETECTING A BREAK IN A PLURALITY OF GLASS FIBERS

[75] Inventors: Frederick M. Shofner, Knoxville, Tenn.; Neil E. Greene, Granville; Terry J. Hanna, Newark, both of Ohio

[73] Assignee: Owens-Corning Fiberglas Corporation, Toledo, Ohio

[21] Appl. No.: 222,110

[22] Filed: Jan. 2, 1981

[51] Int. Cl.³ .......................................... C03B 37/025
[52] U.S. Cl. ..................................... 250/561; 65/10.1
[58] Field of Search ............... 250/561, 222, 571, 572; 65/2, 10.1

[56] References Cited

U.S. PATENT DOCUMENTS 4,229,198 10/1980 Coggin, Jr. et al. ................. 65/10.1
4,319,901 3/1982 Pellegrin et al. ................. 65/10.1 X

*Primary Examiner*—David C. Nelms
*Assistant Examiner*—Darwin R. Hostetter
*Attorney, Agent, or Firm*—Ronald C. Hudgens; Patrick P. Pacella; Ronald E. Champion

[57] ABSTRACT

A method and apparatus for detecting breakage of glass fibers comprising illuminating the fibers with electromagnetic radiation and sensing a variation in the amount of radiation scattered by the fibers as an indication of a break of said fibers.

14 Claims, 7 Drawing Figures

METHOD AND APPARATUS FOR DETECTING A BREAK IN A PLURALITY OF GLASS FIBERS

BACKGROUND OF THE INVENTION

This invention relates to the production of continuous glass fibers, e.g., fibers made by melting particulate batch ingredients or minerals, including basalt and the like, and, more particularly, to a method and apparatus for detecting a break in such fibers during the drawing process.

It is intended that the term "scattered," as used herein, denotes forward scattering, backscattering and right angle scattering of the incident radiation.

It is well known in the art that continuous glass fibers can be produced by attenuating a plurality of streams of molten glass into fibers, collecting the fibers into a strand and winding the strand into a package for subsequent use in manufacturing various products. The molten glass flows from a furnace and through a forehearth into a feeder or bushing which has a plurality of orifices formed therein. The molten glass flows from the orifices as streams which are pulled downwardly at a high rate of speed for attenuation into fibers. A plurality of the attenuated fibers are then gathered together into a strand, coated with a sizing and wound onto a collection tube on a winder collet.

During the fiber forming process, a fiber may break and cause a bead of molten glass to form on the undersurface of the bushing at the orifice at which the breakage occurred. Gradually, the bead of molten glass becomes larger and heavier; the increased weight causes it to fall and contact adjacent fibers which causes them to break. If the spacing between the adjacent orifices is extremely small, the bead of molten glass contacts the adjacent forming cone of molten glass, thus causing more fibers to break. If such breakage is not detected, additional fibers will be broken as the bead continues to grow; this breakage will continue until all of the fibers in the fan are broken. The time required to restart the fiber forming process is related to the number of fibers that have broken. Accordingly, a breakage must be detected as early as possible so that suitable corrective measures can be taken to minimize the downtime of the process.

Therefore, it is an object of this invention to provide a reliable method of and apparatus for detecting breakages in glass fibers during the fiber producing process.

SUMMARY OF THE INVENTION

In accordance with the present invention there is provided a method of detecting breakage of glass fibers, such method comprising the steps of illuminating the fibers with electromagnetic radiation and sensing a variation in the amount of radiation scattered by the fibers as an indication of a break in the fibers.

In addition, the invention provides a glass fiber producing apparatus comprising: a feeder for holding a molten body of thermoplastic material, such feeder having an orificed wall for emitting a plurality of streams of such material; a rotary collector for attenuating the streams into continuous fibers and for winding the fibers into a package; a gathering device located between the feeder and winder for gathering the fibers into a strand before being wound into the package; means for illuminating the fibers with electromagnetic radiation; means for collecting electromagnetic radiation scattered by the fibers; and means responsive to the collected scattered electromagnetic radiation for generating an electrical signal indicative of the amount of light scattered by the fibers. Preferably, the apparatus comprises means for averaging the generated signal over time and means for comparing the averaged signal with a reference signal indicative of the normal amount of radiation scattered by the fibers.

The system of the present invention is well adapted to the fiber forming environment which includes large radiative heat loads from the orificed wall, moisture from prepared sprays and periodic cleaning, binder solids entrained in air circulating around the feeder or bushing, shock-vibration loads due to bushing changes, and similar adverse environmental factors. Moreover, the system does not interfere with normal bushing operation and operator access to the bushing.

In a preferred embodiment, a calibration control is combined with an electro-optical measurement instrument to provide a system having automatic compensation of the entire electro-optical train without interruption of the measurement process for detecting a breakage of the fibers during the fiber forming process. The electro-optical instrument includes a plurality of light-emitting diodes which provide a source of substantially monochromatic electromagnetic radiation and optics for collecting and focusing radiation onto a detector. The radiation is directed through a sampling volume where it impinges upon the fibers that are to be monitored by scattering techniques. The calibration control includes an element rotatably positioned in the path of the electromagnetic radiation, optically upstream of the sampling volume, such that the radiation is periodically blocked and sampled.

Although, the present invention is described herein in a backscattering embodiment, it should be understood that the novel aspects of the invention have much broader application and may be applied to forward and side scattering systems for the detection of breakages in glass fibers.

Other objectives, advantages and applications of the present invention will be made apparent by the following detailed description of the preferred embodiments of the invention.

DETAILED DESCRIPTION OF THE PREFERRED EMBODIMENTS

Figure 1:
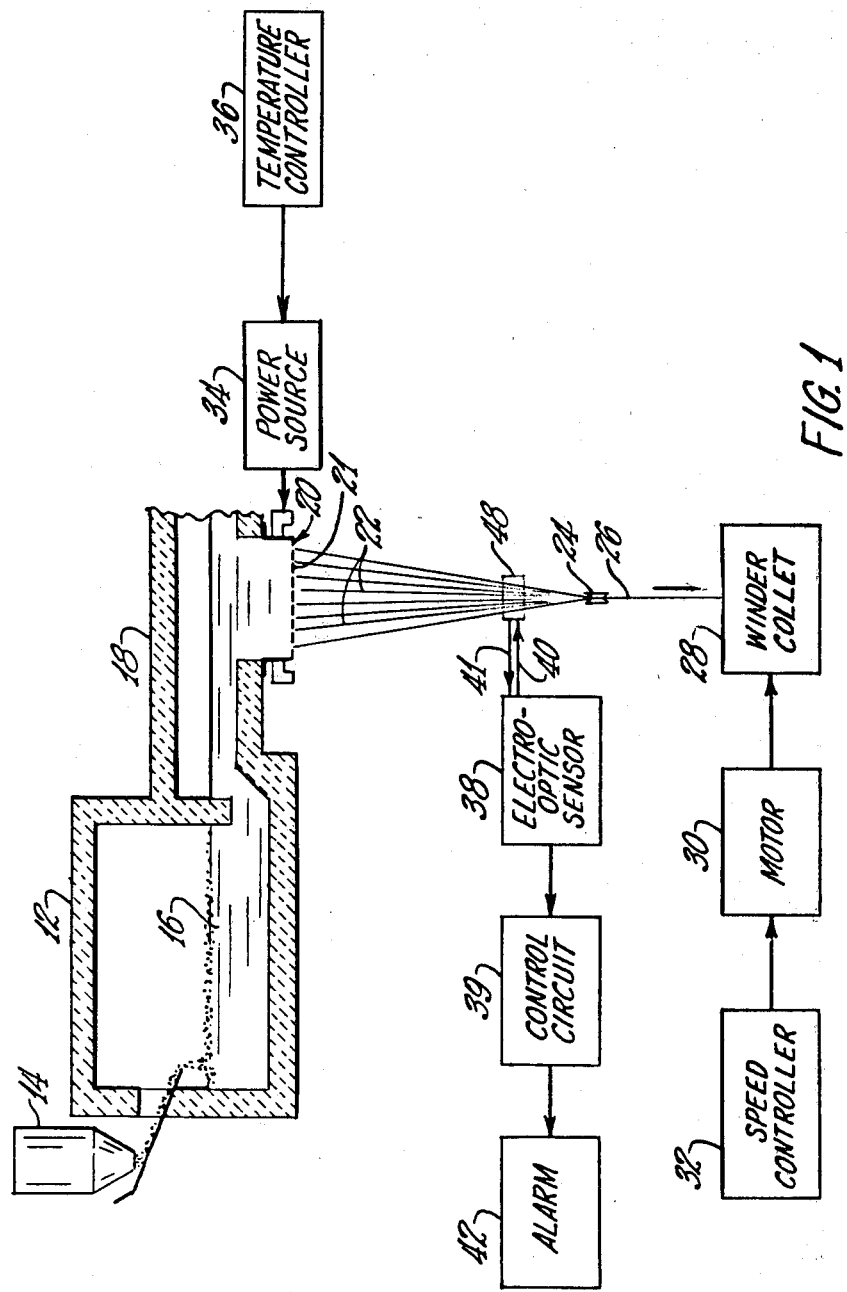
FIG. 1 is a schematic block diagram showing the incorporation of the present invention into an apparatus for producing a plurality of glass fibers.

FIG. 1 shows the incorporation of the present invention into an apparatus for producing a plurality of glass fibers. In a typical fiber forming process, raw materials or batch are provided to a melting furnace 12 by suitable supply means 14 at a rate which is sufficient to maintain the mass flow rate of molten glass 16 being extracted and flowed along forehearth 18 to a fiber forming feeder or bushing 20. From bushing 20, molten glass 16 flows into a plurality of streams through a grid of orifices 21 formed in the bottom of bushing 20, such orifices may have projecting tips or may be tipless. Normally, bushing 20 is electrically heated to control the temperature, thereby controlling the viscosity of the issuing streams of molten glass. The streams of molten glass issuing from orifices 21 are pulled at a high rate of speed for attenuation into individual fibers 22. Attenuated fibers 22 pass downwardly in a generally conical pattern to a gathering member 24 which forms strand 26. Gathering member 24 also may supply a suitable sizing fluid to strand 26 in the known manner, or a separate applicator means may be employed. From gathering member 24, strand 26 moves to a winder collet 28 wherein it is wound on a collection tube to form a package. Winder collet 28 is driven by a motor 30 or any other suitable means and, generally, the speed of motor 30 is regulated by a speed controller 32. A temperature controller 36 regulates the amount of electrical energy provided by power source 34 to heat bushing 20, thereby maintaining bushing 20 at a predetermined temperature.

Electro-optic sensor 38 is positioned between bushing 20 and gathering member 24 such that its emitted beam of light 40, falls upon the unsized fibers of interest in the electro-optically defined sampling volume 48. Emitted light 40 is backscattered from fibers 22 and a portion thereof, which is indicated generally by numeral 41, is collected by sensor 38. Sensor 38 is connected to a control circuit 39 which, in turn, may be connected to an alarm circuit 42 to alert an operator that a break has occurred.

Sampling volume 48 is defined as the joint intersection of the emitted beam of light and the radiation collection optics according to the following equation:

$$I \cdot W = \text{constant}$$

where I is the LED beam intensity in watts/square centimeter and W is the solid angle of reception in steradians. Both I and W are dependent on position relative to the optical system. In essence, sampling volume 48 is that region of space where light from the LED source (numeral 60 in FIGS. 4 and 5) may both fall on fibers 22 and be received by the collection optics (numeral 63 in FIGS. 4 and 5).

Figure 2:
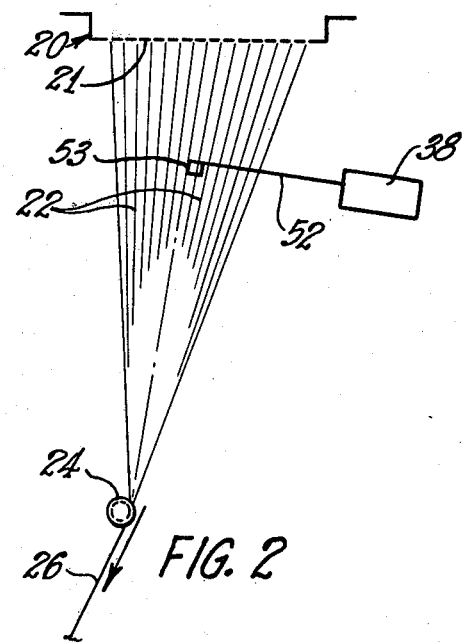
FIG. 2 is a diagrammatic view showing the preferred orientation according to the present invention of a sensor relative to the longitudinal axis of the fibers.

With reference to FIG. 2, the angle between the line of illumination 52 and the fibers of interest 22 should be adjusted so that a maximum amount of light backscattered from preferred fibers will reach the collection optics and be utilized. The amount of emitted light 52 reaching the collection optics is maximized when sensor 38 is tilted on its axis such that emitted light 52 is incident perpendicularly upon the center 53 of the fibers.

Figure 3:
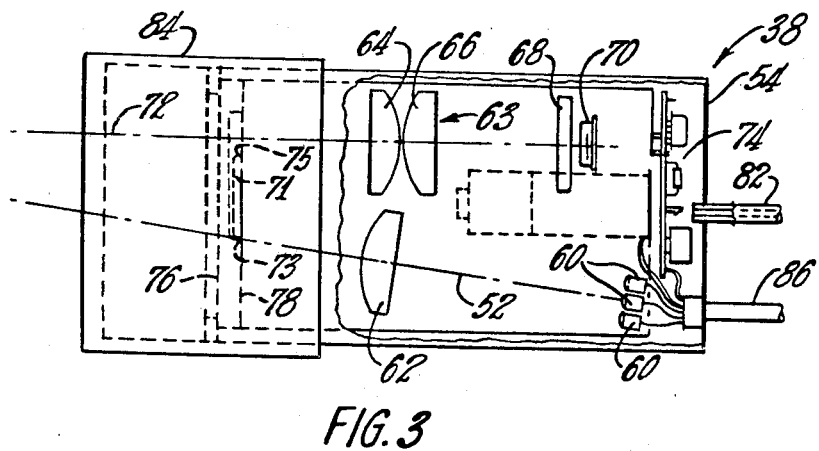
FIG. 3 is a detailed plan view of an apparatus for use with the present invention.
Figure 4:
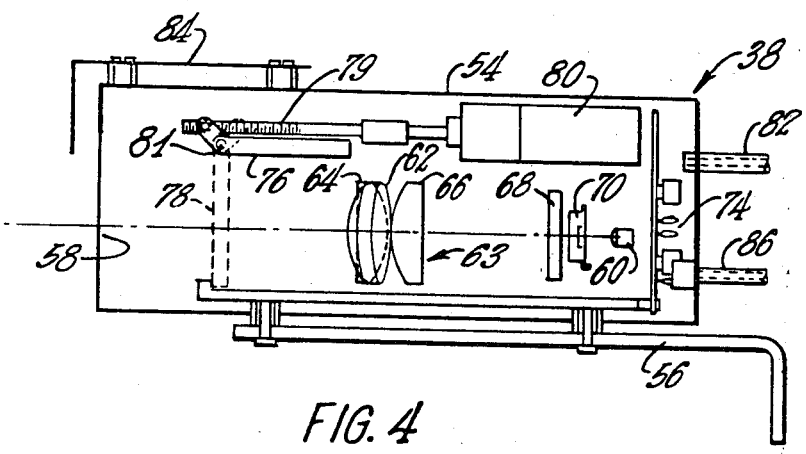
FIG. 4 is a detailed view in elevation of the apparatus shown in FIG. 3.

FIGS. 3 and 4 illustrate one embodiment of electro-optic sensor 38 for use with the present invention from a top view and side view, respectively. Sensor 38 has a housing 54 which is attached by suitable fasteners to mounting plate 56 which, in turn, is mounted in any suitable position adjacent the fiber fan. A quantity of light, indicated by numeral 52, is generated by three light-emitting diodes 60; light 52 from light-emitting diodes 60 is focused into a substantially collimated beam by plano-convex lens 62 after which it exits from housing 54 through aperture 58. Lens 62 is positioned so that its flat side is closest to diodes 60. The collimated beam of monochromatic light may also be generated by a laser or other suitable device. The wavelength of the monochromatic light emitted by diodes 60 may be, for example, 0.9 microns. However, it should be understood that the beam may contain more than one wavelength, in which case, the wavelength or wavelengths of interest would be separated from the collected radiation by conventional filtering techniques.

The light backscattered by the fibers, which is indicated by numeral 72, is passed through collection optics 63 which comprises plano-convex lenses 64 and 66, positioned such that their convex sides are adjacent. Collection optics 63 focuses the backscattered light, after which it passes through an infrared filter 68 onto photodetector 70. The amount of backscattered light received by photodetector 70 is dependent upon the axial response of the system which is related to the focal length of collection optics 63 and the distance of sensor 38 from fibers 22. In the preferred embodiment, the diameter of lens 64 is chosen from the approximate formula which specifies that the arc tangent of the diameter (D) of lens 64 divided by the distance (d) from a plane through the center of lens 64 to the center of sampling volume 48 is greater than or equal to 5° (arc tan $D/d \geq 5°$). The output of photodetector 70 is fed to a preamplifier which is part of electrical circuit 74; circuit 74 also contains a driver circuit for diodes 60.

A calibration element 76 is pivotably mounted on pivotal axis 81 such that it can be moved into a closed position indicated by the dotted lines at numeral 78 so that a calibration of the electro-optical portions of sensor 38 can be performed at predetermined intervals. Calibration element 76 is moved into and out of its closed position by screw drive mechanism 79, which is driven by motor/gearhead 80. Calibration element 76 contains fiber optics 71 with ends 73 and 75. The operation of calibration element 76 is discussed hereinafter in detail.

An air hose or coupling 82 supplies air into housing 54 from an air supply (not shown) for blowing dust particles and the like away from the collection or viewing aperture 58 and for cooling electronic circuit 74 to prevent drift. Sensor 38 is also provided with an L-shaped heat shield 84 to protect it from the heat radiated from the tip plate of bushing 20. Heat shield 84 is attached to the top front part of housing 54 by suitable fasteners such that the short leg of L-shaped heat shield 84 is located in front of housing 54 above aperture 58.

Figure 5:
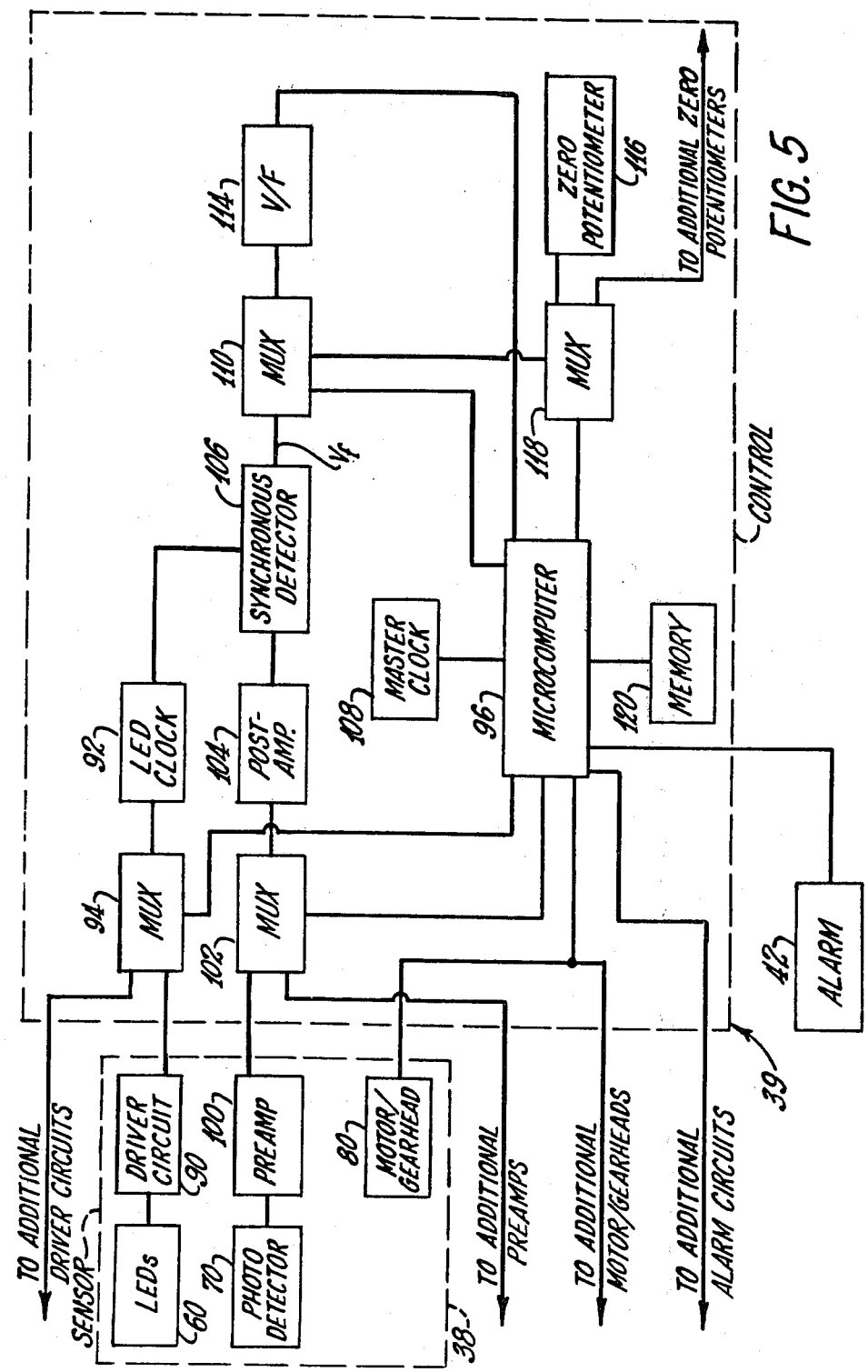
FIG. 5 is a schematic block diagram showing a control system according to the present invention in a microcomputer based system.

With reference to FIG. 5, the signal processing from sensor 38, including how the automatic compensation of gain and zero is implemented by control system 39 in a microcomputer based system, is explained. LEDs 60 are excited by driver circuit 90, which, in turn, is actuated by signals from LED clock 92. The signals from clock 92 reach driver circuit 90 via analog multiplexing switch 94, which is under the control of microcomputer 96. Multiplexing switch 94 may also be connected to other LED driver circuits. Radiation from LEDs 60 is collected by beam forming lens 62, whence it falls upon a representative fiber sample in the electro-optically defined sampling volume 48. Backscattered radiation is received by collection optics 63, passed through infrared filter 68 and focused on photodetector 70. The low level output signal from photodetector 70 is amplified by preamplifier 100 and supplied to multiplexing electronic switch 102 which receives its control signal from microcomputer 96. Multiplexing switch 102 may also be connected to other preamplifiers. Multiplexing switch 102 is connected to postamplifier 104 in which the signal is further amplified and then provided to synchronous detector 106. Clock 92 and synchronous detector 106 are operated in synchronism, as is well known in the art, to permit more reliable signal processing, particularly for low level signals in the presence of high, quasi-static background radiation, such as that found in the vicinity of a luminous bushing.

Synchronous detector 106 filters and applies DC offsets to the signal and provides an output signal, symbolized by $V_f$, to analog multiplexing switch 110 which is under the control of microcomputer 96. Signal $V_f$ is in direct proportion to the amount of light backscattered by the plurality of representative fibers in sampling volume 48. When the output terminal of multiplexing switch 110 is connected to synchronous detector 106, by proper logic from microcomputer 96, $V_f$ is inputted to voltage to frequency converter 114 (V/F converter 114). V/F converter 114 produces an output signal whose frequency is in direct proportion to the analog voltage inputted, this form being optimum for digital processing, as is well known and understood by those skilled in the art.

Signal $V_f$ is compensated for zero and gain variations of the electro-optical system to ensure accurate and reliable results. The variations in the gain of the electro-optical transfer functions can be caused by numerous factors, for example, if the quantity of light produced by the LEDs is reduced by a factor of two, then it follows that the net signal $V_f$ will also be reduced by a factor of two. The gain may also vary if the collection optics are contaminated by foreign matter. For example, if only fifty percent of the light falling upon the collection optics is transmitted, then it follows that the net signal $V_f$ would be reduced by a factor of two. The zero or baseline signal of the system, $V_b$, i.e., the value of $V_f$ when all of the representative fibers in sampling volume 48 are completely removed and no material is inserted in their place, may not reliably approach a true zero voltage but rather some background signal. The origin of $V_b$ may be stray light, ambient light or electromagnetic pickup of any kind.

$V_b$ has been found to be both small and fairly constant and can be made to approach zero by utilizing zero potentiometer 116, which is connected to multiplexing switch 110 by analog multiplexing switch 118 which is under the control of microcomputer 96. Multiplexing switch 118 may be connected to additional zero potentiometers. If $V_b$ should change, it is a simple matter to adjust zero potentiometer 116 so that $V_f$ approaches zero when the fibers to be measured are removed.

The compensation for electro-optical system gain is accomplished by periodically rotating calibration element 76 downward to its closed position 78. Referring to FIGS. 3 and 5, the mechanical operation of calibration element 76 is accomplished by exciting motor/gearhead 80 which, in turn, operates a screw drive mechanism 79 such that calibration element 76 is operated around pivotable axis 81. Motor/gearhead 80 is driven by a signal provided by microcomputer 96. Microcomputer 96 may also provide actuation signals to additional motor/gearheads.

When calibration element 76 is in its closed position 78, the beam of light from LEDs 60 falls on end 73 of fiber optics 71. A precisely known fraction of the incident radiation then emanates from the other end 75 of fiber optics 71, to collection optics 63. The radiation then passes through filter 68 onto photodetector 70 which generates an electric signal. The signal proceeds along the same signal path as a normal signal from the representative fibers in sampling volume 48. Thus, it is evident that the entire electro-optical transfer function is used so that variations in any component ae determined and ultimately compensated.

The signal $V_f$ that is inputted to V/F converter 114 is derived from three conditions: (1) a true signal from representative fibers; (2) a zero signal when no fibers are present; and (3) a calibration signal. All of the signal conditions are produced under the control of microcomputer 96 in accordance with a program determined by program and scratch pad memory 120.

The mathematical operation of automatic compensation of the transfer function implemented by microcomputer 96 to produce an automatically-compensated indication proportional to mean fiber diameter can be generally expressed as follows:

$$V'_f = (V_f - V_b)\frac{V_{ref}}{V_{cal}} \quad (1)$$

where $V'_f$: final, compensated signal which is proportional to the amount of light backscattered by the fibers;

$V_f$: total amount of light backscattered by the fibers in sampling volume 48;

$V_b$: signal with no fibers present;

$V_{ref}$: scaling or multiplying signal; and $V_{cal}$: signal with calibration element 76 in closed position 78.

Clearly, the operation of the apparatus of the present invention in implementing equation (1) is to acquire the total signal $V_f$, subtract off the background $V_b$, multiply by a signal $V_{ref}$, and then divide by the calibration $V_{cal}$. $V_b$ is a reference signal derived from zero potentiometer 116 to make the readings of sensor 38 agree with separately determined calibration values. Evidently, if the transfer function were reduced by a factor of 50%, then the net signal $V_f$ minus $V_b$ would have been reduced by a factor of 2. However, dividing by the calibration signal $V_{cal}$ results in $V'_f$ indicating the same response to the representative fibers in sampling volume 48 as when the transfer function is at its original value.

It has been found that calibration updating of the sensor of approximately once per hour is satisfactory to control the electro-optic transfer function to very precise levels. The initiation of the calibration update is under microcomputer control and in some embodiments takes place at hourly intervals; however, there are other protocols under which the calibration update may be implemented as explained hereinbelow.

The multiplexing functions provided by the various multiplexing switches allow microcomputer 96 to process signals from a plurality of sensors at a single bushing, or a plurality of sensors monitoring a plurality of bushings with one or more sensors monitoring each bushing.

In a typical fiber forming operation, winder collet 28 is brought up to speed after initiation by an operator or by winder speed controller 32. When a predetermined amount of time or, better, weight of glass has been wound onto the package, the run is terminated. At this point, while the new collection tube is being brought into position and a new run started, control circuit 39 receives a signal either from an operator, or from speed controller 32, to go through an automatic calibration. If desired, a protocol may be employed to send the sensor into an automatic calibration, when there is a breakage of the fibers. This protocol will provide the advantages of protecting the internal elements of sensor 38 during the correction of the problem causing the breakage and allowing sensor 38 to utilize downtime for performing the calibration of the transfer function rather than during normal operation.

Microcomputer 96 averages $V_f$ over time to minimize the effects of any transient aberrations in a fiber or fibers, thereby providing a more meaningful signal, $V_{out}$, for detection purposes. By averaging $V_f$ over time, the amount of light backscattered by the fibers is derived from multiple replications of measurements along the lengths of the fibers. Microcomputer 96 then compares $V_{out}$ with a reference signal to determine if less than a predetermined amount of light is being backscattered by the fibers. If $V_{out}$ is less than the reference signal, microcomputer 96 provides a signal to activate alarm 42, thereby alerting an operator that a break has occurred in the fibers.

The reference signal, which must be determined empirically for each process, is chosen to allow for a limited degree of drift in the fiber forming process. Such drift may be caused, for example, by slight changes in winder speed or busing temperature which results in a change in the average diameter of the fibers and hence a change in $V_{out}$. If suitable controls are utilized to stabilize the process, thus producing fibers of uniform diameter, the dead band range may be reduced to a minimum.

In another embodiment, microcomputer 96 also determines the rate of change of $V_{out}$ and compares it with a second reference signal which is indicative of the maximum rate of change of $V_{out}$ allowed before alarm 42 is activated to indicate a break. The second reference signal, as with the first reference signal, must be determined empirically for each process. Therefore, microcomputer 96 activates alarm 42 to signal that a break has occurred if either $V_{out}$ is less than a first reference signal or the rate of change of $V_{out}$ is greater than a second reference signal.

A plurality of sensors may be utilized to monitor a single bushing if the size of the bushing warrants such; the output of each sensor would be provided to microcomputer 96 where it would be processed as described hereinabove.

Figure 6:
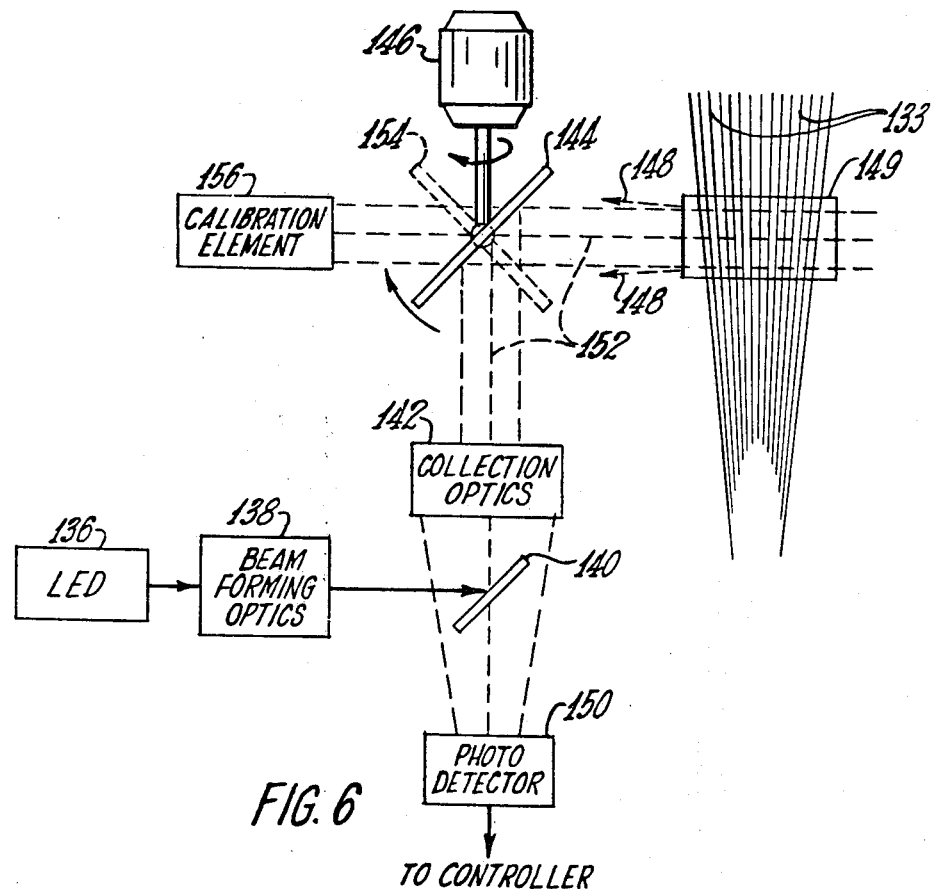
FIG. 6 is a diagrammatic view of an apparatus for use with the present invention that scans the fibers to be monitored.
Figure 7:
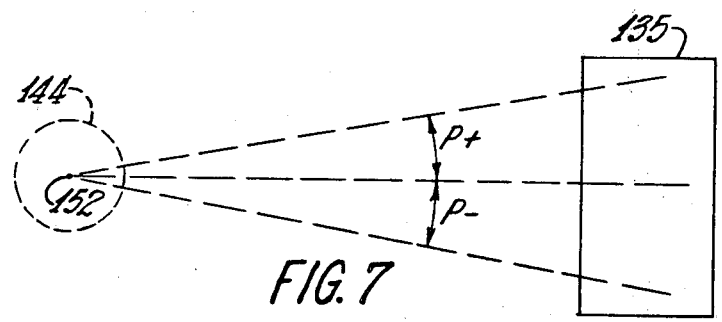
FIG. 7 is a diagrammatic plan view of the apparatus shown in FIG. 6 illustrating the angular orientation of the scanning.

In another embodiment, which is shown diagrammatically in FIGS. 6 and 7, the sensor scans across fibers 133 and generates a signal representative of the radiation backscattered from the fibers. The outside dimensions of the bushing are shown in FIG. 7 by numeral 135. LED 136 provides a quantity of light that is formed into a beam by beam forming optics 138 and brought to bear on beam mirror 140. Beam mirror 140 transmits the beam through collection optics 142 onto scanning mirror 144 which is driven at a rate of about one revolution per second by a small motor 146. Scanning mirror 144 transmits the beam to fibers 133, and backscattered radiation 148 from fibers 133 within sampling volume 149 proceeds coaxially backward to scanning mirror 144 through collection optics 142 onto photodetector 150.

The signals generated by photodetector 150, as scanning mirror 144 sweeps the beam across fibers 133, are then synchronously detected and processed by microcomputer 96. The sensor produces a signal that is a function of the scan angle, which is contained within the limits of $\pm P$ (FIG. 7), as defined by the size of mirror 144 and the distance therefrom to fibers. The signal produced by the sensor is also a function of the fiber axes relative to optical axis 152 of the sensor, as discussed hereinbefore. In this embodiment, microcomputer 96 compares $V_{out}$ with a reference signal to determine if fibers are missing at a particular location, such missing fibers being indicated by a significant change in the magnitude of $V_{out}$. If microcomputer 96 detects a break, it provides a signal to alarm 42 to alert the operator.

When scan mirror 144 has reached the position indicated by numeral 154, the beam impinges upon calibration element 156 from which is precisely known fraction of the incident radiation emanates to scan mirror 144 and then through collection optics 142 onto photodetector 150 for compensation of the transfer function, as discussed above. An electro-optic sensor provides a signal to the controller (control circuit 39 in FIG. 1) to indicate that scan mirror 144 is in its calibrate position 154, thereby causing the microcomputer to enter its calibration routine. Other means can be used for detecting when scan mirror 144 is in its calibration position 154, such as, for example, a microswitch responsive to the position of the shaft of motor 146.

In alternative embodiments, the sensor may scan the sampling volume by pivoting or rotating about an axis, or it may move linearly along the bushing, such as on a conventional pair of rails or tracks.

It is to be understood that variations and modifications of the present invention may be made without departing from the scope of the invention. It is also to be understood that the scope of the invention is not to be interpreted as limited to the specific embodiment disclosed herein, but only in accordance with the appended claims when read in the light of the foregoing disclosure.

What is claimed is:

1. A method of detecting breakage of glass fibers comprising the steps of:
   (a) illuminating a predetermined portion of said fibers in a fiber fan with electromagnetic radiation;
   (b) sensing all of the electromagnetic radiation scattered backwards from the fibers which pass through a predetermined reflection zone;
   (c) generating a first electrical signal, $V_f$, responsive to the amount of electromagnetic radiation sensed when the fibers are present;
   (d) generating a second electrical signal, $V_b$, responsive to the amount of electromagnetic radiation sensed when no fibers are present;
   (e) generating a third electrical signal, $V_{CAL}$, with a calibration device which interconnects the electromagnetic illuminating device of (a) above and the electromagnetic radiation sensing device of (b) above;
   (f) inputting a fourth electrical signal, $V_{ref}$, by suitable exterior switching devices;

(g) using a microcomputer to generate a fifth electrical signal, $V_f'$ from the above signals one through four proportional to the relationship:

$$V_f' = (V_f - V_b)\frac{V_{ref}}{V_{CAL}}$$

(h) integrating said fifth electrical signal $V_f'$ over time to produce a sixth electrical signal $V_{out}$;

(i) comparing the sixth electrical signal $V_{out}$ to a predetermined reference signal to determine when signal $V_{out}$ is less than the reference signal which is an indication of broken fibers; and (j) activating an electrical circuit which alerts the operator when signal $V_{out}$ is less than the reference signal in (i) above to warn of broken fibers.

2. A method as recited in claim 1, wherein the step of illuminating the fibers in a fiber fan is accomplished by directing continuous light from a monochromatic infrared light emitting diode source through lenses to focus the light produced on only a portion of the fibers in the fiber fan.

3. A method as recited in claim 1, wherein the step of sensing the electromagnetic radiation includes focusing the back scattered radiation with lenses, passing this focused radiation through an infrared filter and impinging the focused, filtered light on a photodetector which produces an electrical signal proportional to the quantity of radiation received.

4. A method of detecting breakage of glass fibers comprising the steps of:

(a) illuminating a predetermined portion of said fibers in a fiber fan with electromagnetic radiation;

(b) sensing all of the electromagnetic radiation scattered backwards from the fibers which pass through a predetermined reflection zone;

(c) generating a first electrical signal, $V_f$, responsive to the amount of electromagnetic radiation sensed when the fibers are present;

(d) generating a second electrical signal, $V_b$, responsive to the amount of electromagnetic radiation sensed when no fibers are present;

(e) generating a third electrical signal, $V_{CAL}$, with a calibration device which interconnects the electromagnetic illuminating device of (a) above and the electromagnetic radiation sensing device of (b) above;

(f) inputting a fourth electrical signal, $V_{ref}$, by suitable exterior switching devices;

(g) using a microcomputer to generate a fifth electrical signal, $V_f'$, from the above signals one through four porportional to the relationship:

$$V_f' = (V_f - V_b)\frac{V_{ref}}{V_{CAL}}$$

(h) integrating said fifth electrical signal $V_f'$ over time to produce a sixth signal $V_{out}$;

(i) storing the successive signals $V_{out}$ with the microcomputer to develop a time history of such signals;

(j) comparing each signal $V_{out}$ with previously stored signals as described in (i) above to determine the rate of change of the signal $V_{out}$ with respect to time;

(k) activating an electrical circuit which alerts the operator to broken fibers when the rate of change of the signal $V_{out}$ with respect to time exceeds a predetermined value.

5. A method as recited in claim 4, wherein the step of comparing $V_{out}$ with previously stored signals is accomplished by storing each signal $V_{out}$ which has been integrated over a time period into successive positions in memory with the microcomputer and subtracting the subsequent signal from the previous signal and comparing this difference with a reference signal to determine the rate of change of the signal $V_{out}$.

6. A method as recited in claims 1 or 4, wherein the method further comprises the step of sweeping the beam of electromagnetic radiation across the total fiber fan.

7. An apparatus for producing glass fibers comprising:

(a) a feeder for holding a molten body of thermoplastic material;

(b) the feeder having an orificed bushing for emitting a plurality of streams of thermoplastic material;

(c) a means for heating the bushing;

(d) a means for controlling the environment around the plurality of streams of thermoplastic material below the bushing;

(e) a rotary collector for attenuating the streams into continuous fibers and for winding the fibers into a package;

(f) a gathering device located between the feeder and collector for gathering the fibers into a strand before being wound into the package;

(g) means for illuminating a predetermined portion of the streams of thermoplastic material which forms a fan of glass fibers between the bushing and the rotary collector with electromagnetic radiation;

(h) means for collecting all of the electromagnetic radiation scattered backwards from the fibers which pass through a predetermined reflection zone;

(i) means responsive to the collected scattered electromagnetic radiation for generating a first electrical signal, $V_f$, indicative of the magnitude of the electromagnetic radiation collected when fibers are present;

(j) means responsive to said collected scattered electromagnetic radiation for generating a second electrical signal, $V_b$, indicative of the magnitude of the electromagnetic radiation collected when no fibers are present;

(k) calibration means for shunting a portion of the illuminating electromagnetic radiation directly to the collecting means for generating a third electrical signal, $V_{CAL}$, indicative of the internal response of the electromagnetic transmitting and receiving means;

(l) means for manually inserting a fourth electrical signal, $V_{ref}$, by suitable switching devices;

(m) means for generating a fifth electrical signal, $V_f'$, with a microcomputer from the above signals one through four, proportional to the relationship:

$$V_f' = (V_f - V_b)\frac{V_{ref}}{V_{CAL}}$$

(n) means for generating a sixth electrical signal $V_{out}$ by integrating with the microcomputer the fifth electrical signal, $V_f'$ over time;

(o) means for comparing the sixth signal $V_{out}$ with a predetermined reference signal; and, (p) means for activating an electrical circuit which alerts the operator when the sixth signal $V_{out}$ is less than a predetermined reference signal thus indicating broken fibers.

8. An apparatus as recited in claim 7, wherein the electromagnetic radiation is a collimated beam of continuous monochromatic light.

9. An apparatus as recited in claim 8 wherein the collecting means uses lenses to focus the collected scattered light onto first electrical signal generating means and the first electrical signal generating means comprises a photodetector means responsive to the amount of scattered light focused thereon.

10. An apparatus as recited in claim 7, wherein the apparatus further comprises means for causing the beam to sweep across the fibers.

11. An apparatus for producing glass fibers comprising:

(a) a feeder for holding a molten body of thermoplastic material;

(b) the feeder having an orificed bushing for emitting a plurality of streams of thermoplastic material;

(c) a means for heating the bushing;

(d) a means for controlling the environment around the plurality of streams of thermoplastic material below the bushing;

(e) a rotary collector for attenuating the streams into continuous fibers and for winding the fibers into a package;

(f) a gathering device located between the feeder and collector for gathering the fibers into a strand before being wound into the package;

(g) means for illuminating a predetermined portion of the streams of thermoplastic material which forms a fan of glass fibers with electromagnetic radiation;

(h) means for collecting all of the electromagnetic radiation scattered backwards from the fibers which pass through a predetermined reflection zone;

(i) means responsive to the collected scattered electromagnetic radiation for generating a first electrical signal, $V_f$, indicative of the magnitude of the electromagnetic radiation collected when fibers are present;

(j) means responsive to said collected scattered electromagnetic radiation for generating a second electrical signal, $V_b$, indicative of the magnitude of the electromagnetic radiation collected when no fibers are present;

(k) calibration means for shunting a portion of the illuminating electromagnetic radiation directly to the collecting means for generating a third electrical signal, $V_{CAL}$, indication of the internal response of the electromagnetic transmitting and receiving means;

(l) means for manually inserting a fourth electrical signal, $V_{ref}$, by suitable switching devices;

(m) means for generating a fifth signal, $V_f'$, with a microcomputer from the above signals one through four, proportional to the relationship:

$$V_f' = (V_f - V_b) \frac{V_{ref}}{V_{CAL}}$$

(n) means for generating a sixth signal $V_{out}$ by integrating with the microcomputer the fifth electrical signal, $V_f'$ over time;

(o) means for storing successive sixth signals $V_{out}$ in memory means with the microcomputer to develop a time history of such signals;

(p) means for comparing each signal $V_{out}$ with previously stored signals $V_{out}$ to determine the rate of change of such signals with respect to time;

(q) means for activating an electrical circuit which alerts the operator of a broken fiber when the rate of change with respect to time of signal $V_{out}$ exceeds a predetermined value.

12. An apparatus as recited in claim 11, wherein the electromagnetic radiation is a collimated beam of continuous monochromatic light.

13. An apparatus as recited in claim 11 wherein the collecting means uses lenses to focus the collected scattered light onto first electrical generating means and the first electrical signal generating means comprises a photodetector means responsive to the amount of scattered light focused thereon.

14. An apparatus as recited in claim 11, wherein the apparatus further comprises means for causing the beam to sweep across the fibers.

* * * * *